(12) United States Patent
Kang et al.

(10) Patent No.: US 10,988,424 B2
(45) Date of Patent: Apr. 27, 2021

(54) METHOD FOR PREPARING HALOGEN-SUBSTITUTED STYRENE MONOMER

(71) Applicant: LG Chem, Ltd., Seoul (KR)

(72) Inventors: Byungsoo Kang, Daejeon (KR); Myung Jin Kong, Daejeon (KR); Hyunjik Yi, Daejeon (KR); Wonjae Lee, Daejeon (KR)

(73) Assignee: LG Chem, Ltd.

( * ) Notice: Subject to any disclaimer, the term of this patent is extended or adjusted under 35 U.S.C. 154(b) by 0 days.

(21) Appl. No.: 16/612,088

(22) PCT Filed: Jul. 27, 2018

(86) PCT No.: PCT/KR2018/008563
§ 371 (c)(1),
(2) Date: Nov. 11, 2019

(87) PCT Pub. No.: WO2019/031743
PCT Pub. Date: Feb. 14, 2019

(65) Prior Publication Data
US 2020/0407294 A1    Dec. 31, 2020

(30) Foreign Application Priority Data
Aug. 11, 2017    (KR) ......................... 10-2017-0102462

(51) Int. Cl.
*C07C 17/357*    (2006.01)
(52) U.S. Cl.
CPC ................................ *C07C 17/357* (2013.01)
(58) Field of Classification Search
CPC ........................... C07C 17/357; C07C 69/157
See application file for complete search history.

(56) References Cited

U.S. PATENT DOCUMENTS

| 3,714,275 | A |   | 1/1973  | Pierce et al. |
| 4,230,642 | A |   | 10/1980 | Nishiyama et al. |
| 4,466,904 | A |   | 8/1984  | Watson et al. |
| 5,247,124 | A | * | 9/1993  | Aslam et al. ......... C07C 67/297 |
| 2003/0129622 | A1 |   | 7/2003  | Hellinga et al. |
| 2013/0281449 | A1 |   | 10/2013 | Hurth et al. |

FOREIGN PATENT DOCUMENTS

| CN | 101781161 A | 7/2010 |
| JP | S54115328 A | 9/1979 |
| JP | S61225143 A | 10/1986 |
| JP | 2005502045 A | 1/2005 |
| JP | 2014505688 A | 3/2014 |
| WO | 2014193647 A2 | 12/2014 |

OTHER PUBLICATIONS

Thomas David Yarwood et al., "Synthetic applications of fluorinated phenyllithiums Preparation of fluorinated a-methlstyrenes, benzhydrols, benzophenones and aryltrimethylsilanes", Journal of Fluorine Chemistry, 1996, vol. 78, pp. 113-119.
Das, P. et al. "A direct synethisis of functionalized styrenes and terminal 1,3-dienes via aqueous Wittig chemistry with formalin", Tetrahedron Letters, 2011, vol. 52, pp. 199-201.
Takemoto, M., "Synthesis of styrenes through the decarboxylation of trans-cinnamic acids by plant cell cultures", Tetrahedron Letter, 1999, vol. 40, pp. 6595-6598.
International Search Report from PCT/KR2018/008563 dated Nov. 1, 2018.
Butin, et al, Solvolytic cleavage of 1-(8-quinolyl) ethylmercuric bromide in methanol, M.N. Lomonosov Moscow State University, Feb. 1985, pp. 404-407, No. 2.
Chen, "Optimization of Synthesis Technology of o-Chlorostyrene," Fine Chemical Intermediates, Feb. 2009, pp. 59-61, vol. 39, No. 1, with English abstract.
Japanese Search Report for Application No. 2019563034 dated Oct. 15, 2020, 25 pages.
Kawakami, et al., "Polymers with Oligoorganosiloxane Side Chains as Material for Oxygen Permeable Membranes," Polymer Journal, received Mar. 15, 1985, pp. 1159-1172, vol. 17, No. 11.
Takemoto, et al., "Synthesis of Styrenes through the Biocatalytic Decarboxylation of trans-Cinnamic acids by Plant Cell Cultures," Chemical & Pharmaceutical Bulletin, May 2001, pp. 639-641, vol. 49, No. 5.

* cited by examiner

*Primary Examiner* — Jafar F Parsa
(74) *Attorney, Agent, or Firm* — Lerner, David, Littenberg, Krumholz & Mentlik, LLP

(57) ABSTRACT

The present specification provides a method for preparing a styrene monomer including preparing a styrene monomer of Chemical Formula 2 by reacting a compound represented by Chemical Formula 1 in the presence of phosphoric acid, wherein the phosphoric acid is used in 100 mol % or greater based on 100 mol % of the compound represented by Chemical Formula 1.

15 Claims, 1 Drawing Sheet

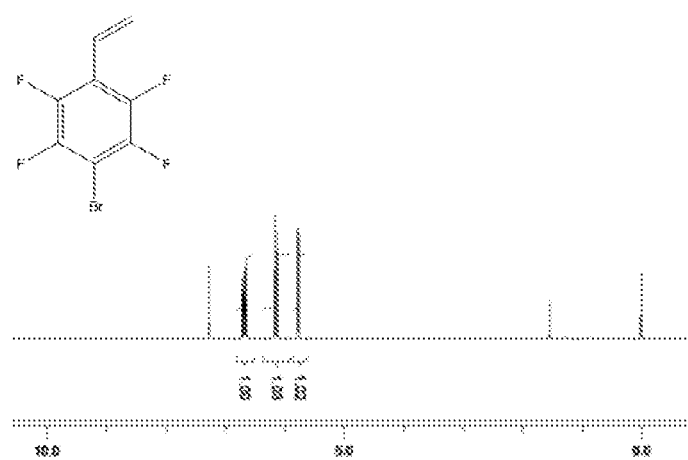

METHOD FOR PREPARING HALOGEN-SUBSTITUTED STYRENE MONOMER

CROSS-REFERENCE TO RELATED APPLICATIONS

The present application is a national phase entry under 35 U.S.C. § 371 of International Application No. PCT/KR2018/008563 filed Jul. 27, 2018, which claims priority from Korean Patent Application No. 10-2017-0102462 filed Aug. 11, 2017, all of which are incorporated herein by reference.

The present specification relates to a method for preparing styrene monomers substituted with halogen.

BACKGROUND ART

The present disclosure relates to a method for preparing styrene monomers. In particular, the present disclosure relates to a method for mass production of halogen-substituted polymers at a competitive price by the reaction with an alcohol as a starting material in phosphoric acid.

Styrene is a key material used for various purposes ranging from the fields of organic synthesis such as medicines or natural products to manufacturing of polystyrene-based resins widely used in everyday lives and industries.

Like polytetrafluoroethylene (PTFE), a polymer compound substituted with halogen has excellent thermal and chemical stability and has excellent mechanical properties, and in order to produce the halogen-substituted polymers at a competitive price, efficient synthetic pathway for monomers is very important. However, with respect to such demands, significantly high production costs and limited availability of monomers is main obstacle restricting the extensive application of halogen-substituted polymers.

DISCLOSURE

Technical Problem

The present application is directed to providing a method for preparing a styrene monomer substituted with halogen.

Technical Solution

One embodiment of the present specification provides a method for preparing a styrene monomer including preparing a styrene monomer of the following Chemical Formula 2 by reacting a compound represented by the following Chemical Formula 1 in the presence of phosphoric acid, wherein the phosphoric acid is used in 100 mol % or greater based on 100 mol % of the compound.

Ar-L-OH           [Chemical Formula 1]

Ar is a phenyl group substituted with one or more halogen groups, and

L is a substituted or unsubstituted alkylene group,

[Chemical Formula 2]

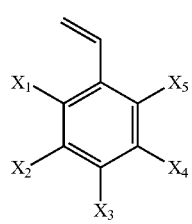

in Chemical Formula 2, at least one of $X_1$ to $X_5$ is a halogen group, and the remaining $X_1$ to $X_5$ are the same as or different from each other, and each independently hydrogen; deuterium; or a halogen group.

Advantageous Effects

A preparation method according to the present disclosure is capable of preparing a styrene monomer having excellent thermal and chemical stability and having excellent mechanical properties by efficiently producing a monomer for mass producing a polymer substituted with halogen at a competitive price.

DESCRIPTION OF DRAWINGS

The FIGURE shows an 1H-NMR spectrum of Compound B according to one embodiment of the present specification.

MODE FOR DISCLOSURE

Herein, the present specification will be described in more detail.

In the present specification, a description of a certain part "including" certain constituents means capable of further including other constituents, and does not exclude other constituents unless particularly stated on the contrary.

In the present specification, a description of one member being placed "on" another member includes not only a case of the one member adjoining the another member but a case of still another member being present between the two members.

Examples of substituents in the present specification are described below, however, the substituents are not limited thereto.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the term "substituted or unsubstituted" means being substituted with one, two or more substituents selected from the group consisting of deuterium; a halogen group; a nitrile group; a nitro group; an imide group; an amide group; a carbonyl group; an ester group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; and a substituted or unsubstituted heterocyclic group, or being substituted with a substituent linking two or more substituents among the substituents illustrated above, or having no substituents. For example, "a substituent linking two or more substituents" may include a biphenyl group. In other words, a biphenyl group may be an aryl group, or interpreted as a substituent linking two phenyl groups.

Existing prior art technologies used for preparing a polymer compound substituted with halogen have limits in that monomer production costs are high and mass production is difficult.

One embodiment of the present specification provides a method for preparing a styrene monomer including preparing a styrene monomer of the following Chemical Formula 2 by reacting a compound represented by the following Chemical Formula 1 in the presence of phosphoric acid, wherein the phosphoric acid is used in 100 mol % or greater based on 100 mol % of the compound represented by Chemical Formula 1.

Ar-L-OH　　　　　　　[Chemical Formula 1]

According to one embodiment of the present specification, Ar is a phenyl group substituted with one or more halogen groups.

According to one embodiment of the present specification, a phenyl group multi-substituted with two or more halogen groups may include halogen groups the same as or different from each other.

In the present specification, the halogen group may be any one of fluorine, chlorine, bromine and iodine.

According to one embodiment of the present specification, L is a substituted or unsubstituted alkylene group.

According to one embodiment of the present specification, L is an alkylene group having 2 to 30 carbon atoms.

According to another embodiment of the present specification, L is an alkylene group having 2 to 15 carbon atoms.

According to another embodiment of the present specification, L is an alkylene group having 2 to 4 carbon atoms.

In the present specification, the alkyl group may be linear or branched, and although not particularly limited thereto, the number of carbon atoms is preferably from 1 to 30. Specific examples thereof may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

In the present specification, the alkylene group means the alkyl group having two bonding sites, that is, a divalent group. Descriptions on the alkyl group provided above may be applied thereto except for each being divalent.

or different from each other, and each independently hydrogen; deuterium; or a halogen group.

For example, $X_1$ to $X_5$ are the same as or different from each other, and may be each independently a halogen group.

According to another embodiment of the present specification, at least one of $X_1$ to $X_5$ is bromine, and the rest may be fluorine.

According to another embodiment of the present specification, one of $X_1$ to $X_5$ is bromine, and the rest may be fluorine.

According to another embodiment of the present specification, $X_3$ of $X_1$ to $X_5$ is bromine, and $X_1$, $X_2$, $X_4$ and $X_5$ may be fluorine.

According to one embodiment of the present specification, the phosphoric acid may be used in 100 mol % or greater based on 100 mol % of the compound represented by Chemical Formula 1. For example, the phosphoric acid may be used in 1500 mol % or greater based on 100 mol % of the compound represented by Chemical Formula 1.

According to another embodiment of the present specification, the phosphoric acid may be used in 100 mol % to 5000 mol % based on 100 mol % of the compound represented by Chemical Formula 1. For example, the phosphoric acid may be used in 1500 mol % to 5000 mol % based on 100 mol % of the compound represented by Chemical Formula 1.

According to another embodiment of the present specification, the phosphoric acid may be used in 1500 mol % to 3000 mol % based on 100 mol % of the compound represented by Chemical Formula 1.

According to one embodiment of the present specification, when the phosphoric acid content is less than 100 mol % based on 100 mol % of the compound represented by Chemical Formula 1, the phosphoric acid just plays a role of a catalyst, which leads to a problem in that a separate solvent needs to be used, and the reaction needs to be progressed under a reduced pressure in order to remove water. However, the content being 100 mol % to 5000 mol % has an advantage in that the synthesis is simply conducted using only phosphoric acid without such an additional solvent and a reduced pressure condition.

In addition, when the phosphoric acid content is from 1500 mol % to 5000 mol %, a yield of the compound of Chemical Formula 2 is at least 70% or higher. However, when the phosphoric acid is used in greater than 5000 mol %, the yield is not enhanced compared to when using the phosphoric acid in 5000 mol % or less, which is disadvantageous in terms of production costs.

According to one embodiment of the present specification, the compound represented by Chemical Formula 1 may be a compound of the following Chemical Formula 3.

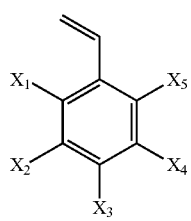

[Chemical Formula 2]

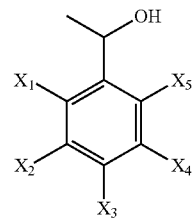

[Chemical Formula 3]

According to one embodiment of the present specification, in Chemical Formula 2, at least one of $X_1$ to $X_5$ is a halogen group, and the remaining $X_1$ to $X_5$ are the same as According to one embodiment of the present specification, in Chemical Formula 3, at least one of $X_1$ to $X_5$ is a halogen group, and the remaining $X_1$ to $X_5$ are the same as or different from each other, and each independently hydrogen; deuterium; or a halogen group.

For example, $X_1$ to $X_5$ are the same as or different from each other, and may be each independently a halogen group.

According to another embodiment of the present specification, at least one of $X_1$ to $X_5$ is bromine, and the rest may be fluorine.

According to another embodiment of the present specification, one of $X_1$ to $X_5$ is bromine, and the rest may be fluorine.

According to another embodiment of the present specification, $X_3$ of $X_1$ to $X_5$ is bromine, and $X_1$, $X_2$, $X_4$ and $X_5$ may be fluorine.

According to one embodiment of the present specification, the compound represented by Chemical Formula 1 may be used in 0.001 M to 20 M, and preferably in 0.01 M to 2 M. A yield generally increases as a reaction size increases, however, the content may be properly adjusted considering reactor capacity.

According to one embodiment of the present specification, the reacting of a compound represented by Chemical Formula 1 may include stirring the compound represented by Chemical Formula and phosphoric acid.

According to another embodiment of the present specification, the stirring may be carried out for 1 hour to 12 hours at 60° C. to 150° C., and more preferably, may be carried out for 2 hours to 5 hours at 130° C. to 150° C.

According to one embodiment of the present specification, the reacting of a compound represented by Chemical Formula 1 may further include adding a stabilizer or an inhibitor. The stabilizer or the inhibitor may include one or more selected from the group consisting of butylcatechol, hydroquinone, butylated hydroxytoluene, butylated hydroxyanisole, phenothiazine, 4-hydroxy-2,2,6,6-tetramethylpiperidine 1-oxyl free radical (4-hydroxy-TEMPO), 2,2-diphenyl-1-picrylhydrazyl free radical (DPPH free radical) and 4-methoxyphenol.

According to one embodiment of the present specification, the stabilizer or the inhibitor may be included in 0.01 mol % to mol % based on 100 mol % of the compound represented by Chemical Formula 1.

According to one embodiment of the present specification, the reacting of a compound represented by Chemical Formula 1 may further include, after the stirring of the compound represented by Chemical Formula 1 and phosphoric acid, cooling the mixture of the compound represented by Chemical Formula 1 and the phosphoric acid.

According to another embodiment of the present specification, the reacting of a compound represented by Chemical Formula 1 may further include removing residues, and the removing of residues may be carried out under vacuum, and may be carried out using one of a distillation method, a column chromatography method or a crystallization method.

Meanwhile, the method for preparing a halogen-substituted styrene monomer according to one embodiment of the present specification is capable of mass producing a styrene monomer substituted with halogen at a competitive price.

Hereinafter, the present specification will be described in detail with reference to examples. However, examples according to the present specification may be modified to various other forms, and the scope of the present specification is not to be construed as being limited to the examples described below. Examples of the present specification are provided in order to more fully describe the present specification to those having average knowledge in the art.

Example 1

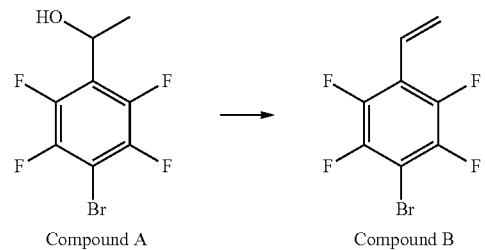

Compound A        Compound B

To a round bottom flask equipped with a magnetic stir bar and a thermostat, Compound A (27.0 g, 98.9 mmol), 4-tert-butylcatechol (1.64 g, 9.89 mmol) and 135 mL of 85% phosphoric acid (1995 mol % with respect to Compound A) were introduced, and the resulting reaction mixture was stirred for 3 hours at 150° C. After cooling the reaction mixture, the residue was distilled in vacuo to give Compound B (79%). Purity of Compound B analyzed by gas chromatography (GC) instrument was at least 98% or higher.

The FIGURE shows an 1H-NMR spectrum of Compound B.

Example 2

Compound B was obtained in a 28% yield using the same method as in Example 1 except that the phosphoric acid content was adjusted to 100 mol % with respect to Compound A.

Example 3

Compound B was obtained in a 77% yield using the same method as in Example 1 except that the phosphoric acid content was adjusted to 1500 mol % with respect to Compound A.

Example 4

Compound B was obtained in a 76% yield using the same method as in Example 1 except that the phosphoric acid content was adjusted to 3000 mol % with respect to Compound A.

Example 5

Compound B was obtained in a 72% yield using the same method as in Example 1 except that the phosphoric acid content was adjusted to 5000 mol % with respect to Compound A.

Comparative Example 1

The reaction for compound B was conducted using the same method as in Example 1 except that the phosphoric acid content was adjusted to 10 mol % with respect to Compound A, however, the reaction was not progressed at all, and a target product was not able to be obtained.

Comparative Example 2

The reaction for compound B was conducted using the same method as in Example 1 except that the phosphoric acid content was adjusted to 50 mol % with respect to Compound A, however, the reaction rate was very low, and the conversion rate identified using a GC analysis device after 12 hours was less than 10%.

Comparative Example 3

Compound B was obtained using the same method as in Example 1 except that the phosphoric acid content was adjusted to 5985 mol % with respect to Compound A, however, the yield was 72%, which was no significant enhancement.

Comparative Example 4

The reaction for compound B was conducted using the same method as in Example 1 except that concentrated sulfuric acid was used in 10 mol % instead of phosphoric acid, however, ether by-products produced by dehydration from Compound A were produced in large quantities.

Comparative Example 5

The reaction for compound B was conducted using the same method as in Example 1 except that concentrated sulfuric acid was used in 50 mol % instead of phosphoric acid, however, ether by-products produced by dehydration from Compound A were produced in large quantities.

Comparative Example 6

The reaction for compound B was conducted using the same method as in Example 1 except that toluenesulfonic acid was used in 10 mol % instead of phosphoric acid, however, ether by-products produced by dehydration from Compound A were produced in large quantities.

Comparative Example 7

The reaction for compound B was conducted using the same method as in Example 1 except that toluenesulfonic acid was used in 50 mol % instead of phosphoric acid, however, ether by-products produced by dehydration from Compound A were produced in large quantities.

Comparative Example 8

The reaction for compound B was conducted using the same method as in Example 1 except that concentrated hydrochloric acid was used in 10 mol % instead of phosphoric acid, however, the reaction was not progressed.

Comparative Example 9

The reaction for compound B was conducted using the same method as in Example 1 except that concentrated hydrochloric acid was used in 50 mol % instead of phosphoric acid, however, the reaction was not progressed.

The invention claimed is:
1. A method for preparing a styrene monomer comprising:
preparing a styrene monomer of the following Chemical Formula 2 by reacting a compound represented by the following Chemical Formula 3 in the presence of phosphoric acid,
wherein the phosphoric acid is used in 100 mol % or greater based on 100 mol % of the compound represented by the following Chemical Formula 3:

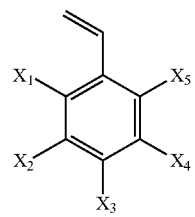

[Chemical Formula 2]

in Chemical Formula 2,
at least one of $X_1$ to $X_5$ is a halogen group; and
the remaining $X_1$ to $X_5$ are the same as or different from each other, and each independently hydrogen; deuterium; or a halogen group,

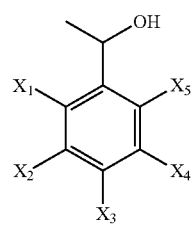

[Chemical Formula 3]

in Chemical Formula 3,
at least one of $X_1$ to $X_5$ is a halogen group; and
the remaining $X_1$ to $X_5$ are the same as or different from each other, and each independently hydrogen; deuterium; or a halogen group.

2. The method for preparing a styrene monomer of claim 1, wherein the phosphoric acid is used in 100 mol % to 5000 mol % based on 100 mol % of the compound represented by Chemical Formula 3.

3. The method for preparing a styrene monomer of claim 1, wherein the compound represented by Chemical Formula 3 is used in 0.001 M to 20 M.

4. The method for preparing a styrene monomer of claim 1, further comprising adding a stabilizer or an inhibitor.

5. The method for preparing a styrene monomer of claim 4, wherein the stabilizer or the inhibitor includes one or more selected from the group consisting of butylcatechol, hydroquinone, butylated hydroxytoluene, butylated hydroxyanisole, phenothiazine, 4-hydroxy-2,2,6,6-tetramethylpiperidine 1-oxyl free radical (4-hydroxy-TEMPO), 2,2-diphenyl-1-picrylhydrazyl free radical (DPPH free radical) and 4-methoxyphenol.

6. The method for preparing a styrene monomer of claim 1, wherein in Chemical Formulas 2 and 3, the halogen group is each independently fluorine, chlorine, bromine or iodine.

7. The method for preparing a styrene monomer of claim 1, wherein in Chemical Formula 2, X3 is bromine, and X1, X2, X4 and X5 are fluorine.

8. The method for preparing a styrene monomer of claim 1, wherein in Chemical Formula 3, X3 is bromine, and X1, X2, X4 and X5 are fluorine.

9. The method for preparing a styrene monomer of claim 1, further comprising stirring the compound represented by Chemical Formula 3 and the phosphoric acid.

10. The method for preparing a styrene monomer of claim 9, wherein the stirring is carried out for 1 hour to 12 hours at 60° C. to 150° C.

11. The method for preparing a styrene monomer of claim 4, wherein the stabilizer or the inhibitor is included in 0.01 mol % to 20 mol % based on 100 mol % of the compound represented by Chemical Formula 3.

12. The method for preparing a styrene monomer of claim 1, further comprising cooling the mixture of the compound represented by Chemical Formula 3 and the phosphoric acid.

13. The method for preparing a styrene monomer of claim 1, further comprising removing residues.

14. The method for preparing a styrene monomer of claim 13, wherein the removing of residues is carried out under vacuum.

15. The method for preparing a styrene monomer of claim 13, wherein the removing of residues is carried out using one of a distillation method, a column chromatography method or a crystallization method.

* * * * *